(12) United States Patent
Mitsuda et al.

(10) Patent No.: US 11,224,560 B2
(45) Date of Patent: Jan. 18, 2022

(54) COMPOSITION COMPRISING AN ASSOCIATIVE THICKENER

(71) Applicant: L'OREAL, Paris (FR)

(72) Inventors: Shinobu Mitsuda, Kawasaki (JP); Makoto Saito, Kawasaki (JP)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/738,883

(22) PCT Filed: Jul. 26, 2016

(86) PCT No.: PCT/JP2016/072462
§ 371 (c)(1),
(2) Date: Dec. 21, 2017

(87) PCT Pub. No.: WO2017/018541
PCT Pub. Date: Feb. 2, 2017

(65) Prior Publication Data
US 2018/0168974 A1    Jun. 21, 2018

(30) Foreign Application Priority Data
Jul. 29, 2015 (JP) ............................. JP2015-149542

(51) Int. Cl.
*A61K 8/39* (2006.01)
*A61K 8/19* (2006.01)
(Continued)

(52) U.S. Cl.
CPC .................. *A61K 8/39* (2013.01); *A61K 8/19* (2013.01); *A61K 8/345* (2013.01); *A61K 8/365* (2013.01);
(Continued)

(58) Field of Classification Search
None
See application file for complete search history.

(56) References Cited

U.S. PATENT DOCUMENTS

| | | | |
|---|---|---|---|
| 2009/0318550 A1* | 12/2009 | Mallard | A61Q 19/08 514/533 |
| 2012/0183492 A1* | 7/2012 | Tominaga | A61K 8/365 424/78.03 |

(Continued)

FOREIGN PATENT DOCUMENTS

| | | | |
|---|---|---|---|
| FR | 2954125 A1 | 6/2011 | |
| FR | 3006187 A1 | 12/2014 | |

(Continued)

OTHER PUBLICATIONS

Korean Office Action for counterpart Application No. KR-2017-7036452, dated Feb. 25, 2019 with translation.

(Continued)

*Primary Examiner* — Kyung S Chang
(74) *Attorney, Agent, or Firm* — The Marbury Law Group, PLLC

(57) ABSTRACT

The present invention relates to a composition, preferably a cosmetic composition for a keratin substance, preferably skin, comprising: (a) at least one associative thickener; (b) at least one specific alkyleneoxide derivative; (c) at least one nonionic surfactant, other than (b), with an HLB value of 13.0 or less; and (d) water. The composition according to the present invention can prevent soaping and can provide excellent texture, when used, while providing sufficient thickening or gelling effects.

16 Claims, 1 Drawing Sheet

(51) Int. Cl.
*A61K 8/892* (2006.01)
*A61K 8/34* (2006.01)
*A61K 8/90* (2006.01)
*A61K 8/86* (2006.01)
*A61K 8/87* (2006.01)
*A61Q 19/00* (2006.01)
*A61K 8/365* (2006.01)

(52) U.S. Cl.
CPC .............. *A61K 8/86* (2013.01); *A61K 8/87* (2013.01); *A61K 8/892* (2013.01); *A61K 8/90* (2013.01); *A61Q 19/00* (2013.01); *A61K 2800/10* (2013.01); *A61K 2800/48* (2013.01); *A61K 2800/548* (2013.01); *A61K 2800/594* (2013.01); *A61K 2800/5922* (2013.01)

(56) References Cited

U.S. PATENT DOCUMENTS

| | | |
|---|---|---|
| 2012/0322876 A1 | 12/2012 | Kermorvan et al. |
| 2015/0335538 A1* | 11/2015 | Bernard ............... A61Q 1/00 424/401 |
| 2016/0101041 A1 | 4/2016 | D'Arras et al. |

FOREIGN PATENT DOCUMENTS

| | | | |
|---|---|---|---|
| JP | 2006-232717 A | 9/2006 | |
| JP | 2008-266218 A | 11/2008 | |
| JP | 2011-032273 A | 2/2011 | |
| JP | 2014-122199 A | 7/2014 | |
| KR | 10-0613969 B1 | 8/2006 | |
| KR | 10-2010-0002124 A | 1/2010 | |
| WO | WO-2014098265 A1 * | 6/2014 | ............... A61K 8/39 |
| WO | WO-2014111571 A1 * | 7/2014 | ............... A61K 8/06 |

OTHER PUBLICATIONS

International Search Report from the European Patent Office in International Application No. PCT/JP2016/072462 dated Sep. 28, 2016.

Written Opinion of the International Searching Authority from the European Patent Office in International Application No. PCT/JP2016/072462 dated Oct. 12, 2016.

Japanese Office Action for counterpart Application No. 2015-149542, dated Apr. 8, 2019, with English Translation.

* cited by examiner

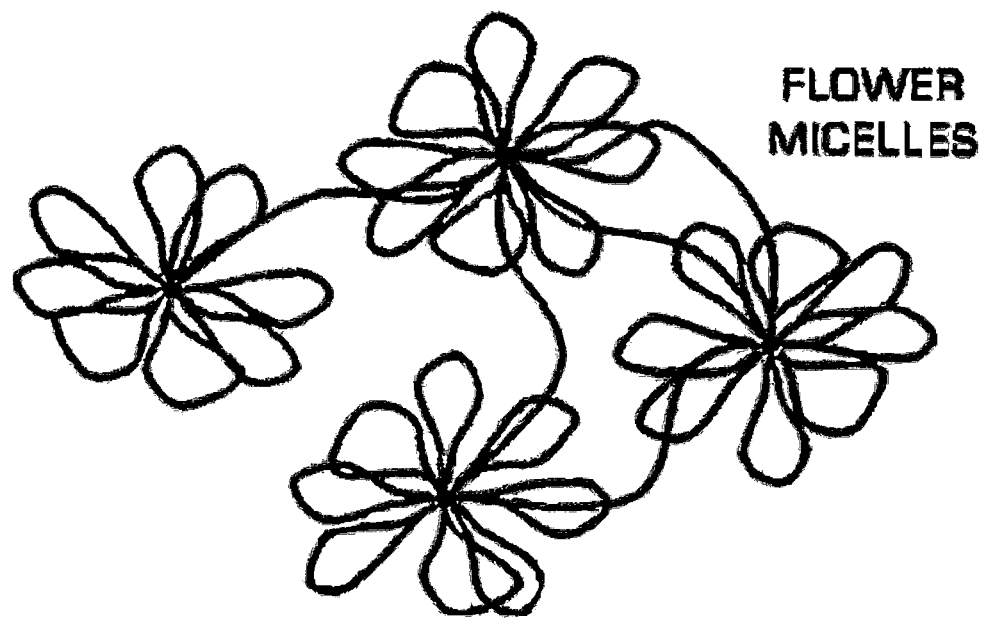

COMPOSITION COMPRISING AN ASSOCIATIVE THICKENER

CROSS REFERENCE TO RELATED APPLICATIONS

This is a national stage application of PCT/EP2016/072462, filed internationally on Jul. 26, 2016, which claims priority to Japanese Application No. 2015-149542, filed on Jul. 29, 2015, both of which are incorporated by reference herein in their entireties.

TECHNICAL FIELD

The present invention relates to a composition, in particular a cosmetic composition, for a keratin substance such as skin.

BACKGROUND ART

The thickening or gelation of aqueous media with polymers has been the subject of research for a long time, especially in the cosmetic and pharmaceutical industries. In some cosmetic and pharmaceutical compositions, an associative thickener has been used for thickening and/or gelling the compositions.

The associative thickener is capable of reversibly associating with itself or with other molecules or particles. This physical association can give rise to thixotropic or shear-thinning macromolecular systems, i.e. systems whose viscosity depends on the shear forces to which they are subjected.

However, the use of an associative thickener may pose a certain number of problems, such as a rather unpleasant texture.

Furthermore, an associative thickener may cause soaping (foaming) on application, when it is used for an aqueous medium to prepare a transparent gel. The soaping is not preferable, because the foam prepared looks white and this appearance does not leave a good impression on consumers.

DISCLOSURE OF INVENTION

An objective of the present invention is to provide a composition, preferably a cosmetic composition for a keratin substance, such as skin, which can prevent soaping and can provide excellent texture, when used, while providing sufficient thickening or gelling effects.

The above objective of the present invention can be achieved by a composition comprising:
(a) at least one associative thickener;
(b) at least one alkyleneoxide derivative represented by the following chemical formula (I):

  (I)

wherein
Z denotes a residue obtained by removing hydroxyl group(s) from a compound having 3 to 9 hydroxyl groups;
AO denotes an oxyalkylene group having 3 to 4 carbon atoms;
EO denotes an oxyethylene group;
BO denotes an oxyalkylene group having 4 carbon atoms;
a denotes 3 to 9;
l, m, and n denote the average addition mole numbers of AO, EO and BO, respectively, and $1 \leq l \leq 50$, $1 \leq m \leq 50$ and $0.5 \leq n \leq 5$;
a weight ratio of AO to EO (AO/EO) ranges from 1/5 to 5/1; and
AO and EO may have been added randomly or in the form of blocks;
(c) at least one nonionic surfactant, other than (b), with an HLB value of 13.0 or less; and
(d) water.

The (a) associative thickener may be an associative polymeric thickener, preferably an associative polyurethane thickener.

The (a) associative thickener may preferably be a nonionic associative polyurethane/polyether which has both at least one hydrophilic moiety and at least one hydrophobic moiety.

The (a) associative thickener may be selected from polyurethane/polyethers comprising in their chain at least one polyoxyethylenated hydrophilic block and at least one of hydrophobic blocks containing at least one sequence chosen from aliphatic sequences, cycloaliphatic sequences, and aromatic sequences, preferably polyurethane/polyethers comprising at least two hydrocarbon-based lipophilic chains having from 8 to 30 carbon atoms, separated by a hydrophilic block, and wherein the hydrocarbon-based chains are chosen from pendent chains and chains at the end of the hydrophilic block, and more preferably Steareth-100/PEG-136/HDI Copolymer, PEG-240/HDI Copolymer Bis-decyltetradeceth-20 ether, and mixtures thereof.

The amount of the (a) associative thickener in the composition may be from 0.01 to 10% by weight, preferably from 0.1 to 5% by weight, and more preferably from 0.3 to 1% by weight, relative to the total weight of the composition.

The (b) alkyleneoxide derivative may be represented by the following chemical formula (II):

  (II)

wherein
Gly denotes a residue obtained by removing hydroxyl groups from glycerin;
PO denotes an oxypropylene group;
EO denotes an oxyethylene group;
s and t denote the average addition mole numbers of PO and EO, respectively, and have a value ranging from 1 to 50;
the weight ratio of PO to EO (PO/EO) ranges from 1/5 to 5/1;
BO denotes an oxyalkylene group having 4 carbon atoms; and
u denotes the average addition mole number of BO, and ranges from 0.5 to 5.

The amount of the (b) alkyleneoxide derivative in the composition may be from 0.01 to 10% by weight, preferably from 0.1 to 5% by weight, and more preferably from 0.5 to 2% by weight, relative to the total weight of the composition.

The (c) nonionic surfactant with an HLB value of 13.0 or less may be selected from:
(1) (1-40 EO) and polyoxypropylenated (5-30 PO) alkyl ($C_{16}$-$C_{30}$) ethers, and preferably (15-40 EO) and polyoxypropylenated (5-30 PO) alkyl ($C_{16}$-$C_{24}$) ethers;
(2) mono- or polyoxyethylenated fatty ethers/esters, preferably polyoxyethylenated fatty esters, and more preferably polyoxyethylenated $C_8$-$C_{40}$ fatty ester having a polyoxyethylene moiety derived from 2 to 100 polyoxyethylenes;

(3) mono- or polyglycerolated fatty ethers/esters, preferably polyglycerolated fatty esters, and more preferably polyglycerolated $C_8$-$C_{40}$ fatty ester having a polyglycerol moiety derived from 2 to 10 glycerols; and (4) silicone surfactants, preferably dimethicone copolyol.

The amount of the (c) nonionic surfactant with an HLB value of 13.0 or less in the composition may be from 0.01 to 10% by weight, preferably from 0.05 to 5% by weight, and more preferably from 0.1 to 2% by weight, relative to the total weight of the composition.

The amount of the (d) water in the composition may be from 50 to 95% by weight, preferably from 60 to 90% by weight, and more preferably from 70 to 90% by weight, relative to the total weight of the composition.

The viscosity of the composition may be 530 mPa·s or more, preferably 550 mPa·s or more, and more preferably 580 mPa·s or more.

It is preferable that the composition according to the present invention be in the form of a gel, and more preferably a transparent gel.

The composition according to the present invention may be a cosmetic composition, preferably a cosmetic composition for a keratin substance, and more preferably a skin cosmetic composition.

The present invention also relates to a cosmetic process for a keratin substance such as skin, comprising the step of: applying onto the keratin substance the composition according to the present invention.

BRIEF DESCRIPTION OF DRAWINGS

FIG. 1 shows a front view of an example of a network formed by an associative polyurethane thickener in water in which the hydrophobic parts of the associative polyurethane thickener connects to form quasi-micelles which are indicated as flower micelles.

BEST MODE FOR CARRYING OUT THE INVENTION

After diligent research, the inventors have found that the use of an alkyleneoxide derivative and a specific nonionic surfactant in combination with an associative thickener can prevent soaping caused by the associative thickener and can provide excellent texture, while providing sufficient thickening or gelling effects.

Thus, the composition, preferably a cosmetic composition for keratin substance, preferably skin, according to the present invention comprises:

(a) at least one associative thickener;
(b) at least one alkyleneoxide derivative represented by the following chemical formula (I):

wherein
Z denotes a residue obtained by removing hydroxyl group(s) from a compound having 3 to 9 hydroxyl groups;
AO denotes an oxyalkylene group having 3 to 4 carbon atoms;
EO denotes an oxyethylene group;
BO denotes an oxyalkylene group having 4 carbon atoms;
a denotes 3 to 9;
l, m, and n denote the average addition mole numbers of AO, EO and BO, respectively, and $1 \leq l \leq 50$, $1 \leq m \leq 50$ and $0.5 \leq n \leq 5$;
a weight ratio of AO to EO (AO/EO) ranges from 1/5 to 5/1; and
AO and EO may have been added randomly or in the form of blocks;

(c) at least one nonionic surfactant, other than (b), with an HLB value of 13.0 or less; and
(d) water.

The composition according to the present invention can prevent soaping and can provide excellent texture, when used, while providing sufficient thickening or gelling effects.

Hereafter, the composition according to the present invention and the process according to the present invention will each be described in a detailed manner.

[Composition]

The composition according to the present invention comprises:
(a) at least one associative thickener;
(b) at least one alkyleneoxide derivative represented by the following chemical formula (I):

wherein
Z denotes a residue obtained by removing hydroxyl group(s) from a compound having 3 to 9 hydroxyl groups;
AO denotes an oxyalkylene group having 3 to 4 carbon atoms;
EO denotes an oxyethylene group;
BO denotes an oxyalkylene group having 4 carbon atoms;
a denotes 3 to 9;
l, m, and n denote the average addition mole numbers of AO, EO and BO, respectively, and $1 \leq l \leq 50$, $1 \leq m \leq 50$ and $0.5 \leq n \leq 5$;
a weight ratio of AO to EO (AO/EO) ranges from 1/5 to 5/1; and
AO and EO may have been added randomly or in the form of blocks;

(c) at least one nonionic surfactant, other than (b), with an HLB value of 13.0 or less; and
(d) water.

It is preferable that the composition according to the present invention be a cosmetic composition, in particular a cosmetic composition for a keratin substance such as skin.

(Associative Thickener)

The composition according to the present invention comprises (a) at least one associative thickener. Two or more (a) associative thickeners may be used in combination. Thus, a single type of associative thickener or a combination of different types of associative thickener may be used.

As used herein, the expression "associative thickener" means an amphiphilic thickener comprising both hydrophilic units and hydrophobic units, for example, at least one $C_8$-$C_{30}$ fatty chain and at least one hydrophilic unit.

Representative associative thickeners that may be used are associative polymers chosen from:

(1) nonionic amphiphilic polymers comprising at least one fatty chain and at least one hydrophilic unit;
(2) anionic amphiphilic polymers comprising at least one hydrophilic unit and at least one fatty-chain unit;
(3) cationic amphiphilic polymers comprising at least one hydrophilic unit and at least one fatty-chain unit; and
(4) amphoteric amphiphilic polymers comprising at least one hydrophilic unit and at least one fatty-chain unit, wherein the fatty chain unit contains from 10 to 30 carbon atoms.

The (1) nonionic amphiphilic polymers comprising at least one fatty chain unit and at least one hydrophilic unit may, for example, be chosen from:
  (i) celluloses modified with groups comprising at least one fatty chain; examples that may be mentioned include:
    hydroxyethylcelluloses modified with groups comprising at least one fatty chain chosen from alkyl, arylalkyl and alkylaryl groups, and in which the alkyl groups are, for example, $C_8$-$C_{22}$, such as the product Natrosol Plus Grade 330 CS($C_1$-$C_6$ alkyls) sold by the company Aqualon, and the product Bermocoll EHM 100 sold by the company Berol Nobel, and
    celluloses modified with polyalkylene glycol alkylphenyl ether groups, such as the product Amercell Polymer HM-1500 (polyethylene glycol (15) nonylphenyl ether) sold by the company Amerchol;
  (ii) hydroxypropyl guars modified with groups comprising at least one fatty chain, such as the product Esaflor HM 22 ($C_{22}$ alkyl chain) sold by the company Lamberti, and the products Miracare XC95-3 ($C_{14}$ alkyl chain) and RE205-1 ($C_{20}$ alkyl chain) sold by the company Rhodia Chimie;
  (iii) polyether urethanes comprising at least one fatty chain, such as $C_{10}$-$C_{30}$ alkyl or alkenyl groups, for instance the products Elfacos T 210 and Elfacos T 212 sold by the company Akzo or the products Aculyn 44 and Aculyn 46 sold by the company Rohm & Haas;
  (iv) copolymers of vinylpyrrolidone and of hydrophobic fatty-chain monomers; examples that may be mentioned include:
    the products Antaron V216 and Ganex V216 (vinylpyrrolidone/hexadecene copolymer) sold by the company I.S.P., and
    the products Antaron V220 and Ganex V220 (vinylpyrrolidone/eicosene copolymer) sold by the company I.S.P.;
  (v) copolymers of $C_1$-$C_6$ alkyl acrylates or methacrylates and of amphiphilic monomers comprising at least one fatty chain, such as the oxyethylenated methyl methacrylate/stearyl acrylate copolymer sold by the company Goldschmidt under the name Antil 208;
  (vi) copolymers of hydrophilic acrylates or methacrylates and of hydrophobic monomers comprising at least one fatty chain, such as polyethylene glycol methacrylate/lauryl methacrylate copolymer.

The (2) anionic amphiphilic polymers comprising at least one hydrophilic unit and at least one fatty-chain unit, may, for example, be chosen from those comprising at least one fatty-chain allyl ether unit and at least one hydrophilic unit comprising an ethylenic unsaturated anionic monomeric unit, for example, a vinylcarboxylic acid unit and further, for example, be chosen from units derived from acrylic acids, methacrylic acids and mixtures thereof, wherein the fatty-chain allyl ether unit corresponds to the monomer of formula (I) below:

$$CH_2=C(R_1)CH_2OB_nR \qquad (I)$$

in which $R_1$ is chosen from H and $CH_3$, B is an ethyleneoxy radical, n is chosen from zero and integers ranging from 1 to 100, R is chosen from hydrocarbon-based radicals chosen from alkyl, arylalkyl, aryl, alkylaryl and cycloalkyl radicals, containing from 10 to 30 carbon atoms, and further, for example, from 10 to 24 carbon atoms and even further, for example, from 12 to 18 carbon atoms.

In one embodiment, a unit of formula (I) is, for example, a unit in which $R_1$ can be H, n can be equal to 10, and R can be a stearyl ($C_{18}$) radical.

Anionic amphiphilic polymers of this type are described and prepared, according to an emulsion polymerization process, in patent EP-0 216 479 B2.

In one embodiment, anionic amphiphilic polymers are, for example, polymers formed from 20% to 60% by weight of acrylic acid and/or of methacrylic acid, from 5% to 60% by weight of lower alkyl (meth)acrylates, from 2% to 50% by weight of fatty-chain allyl ether of formula (I), and from 0% to 1% by weight of a crosslinking agent which is a well-known copolymerizable unsaturated polyethylenic monomer, for example, diallyl phthalate, allyl(meth)acrylate, divinylbenzene, (poly)ethylene glycol dimethacrylate and methylenebisacrylamide.

Examples of such polymers are crosslinked terpolymers of methacrylic acid, of ethyl acrylate and of polyethylene glycol (10 EO) stearyl ether (Steareth-10), such as those sold by the company Ciba under the names Salcare SC 80 and Salcare SC 90, which are aqueous 30% emulsions of a crosslinked terpolymer of methacrylic acid, of ethyl acrylate and of steareth-10 allyl ether (40/50/10).

The anionic amphiphilic polymers may further be chosen, for example, from those comprising at least one hydrophilic unit of unsaturated olefinic carboxylic acid type, and at least one hydrophobic unit of a type such as a ($C_{10}$-$C_{30}$) alkyl ester of an unsaturated carboxylic acid. The hydrophilic unit of unsaturated olefinic carboxylic acid type corresponds to, for example, the monomer of formula (II) below:

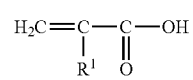

(II)

in which $R^1$ is chosen from H, $CH_3$ and $C_2H_5$, i.e. acrylic acid, methacrylic acid and ethacrylic acid units. The hydrophobic unit of a type such as a ($C_{10}$-$C_{30}$) alkyl ester of an unsaturated carboxylic acid corresponds to, for example, the monomer of formula (III) below:

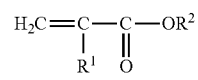

(III)

in which $R^1$ is chosen from H, $CH_3$ and $C_2H_5$ (i.e. acrylate, methacrylate and ethacrylate units) and is, for example, chosen from H (acrylate units) and $CH_3$ (methacrylate units), $R^2$ is chosen from $C_{10}$-$C_{30}$ alkyl radicals, for example, $C_{12}$-$C_{22}$ alkyl radicals.

Examples of ($C_{10}$-$C_{30}$)alkyl esters of unsaturated carboxylic acids include lauryl acrylate, stearyl acrylate, decyl acrylate, isodecyl acrylate, and dodecyl acrylate, and the corresponding methacrylates, lauryl methacrylate, stearyl methacrylate, decyl methacrylate, isodecyl methacrylate and dodecyl methacrylate.

Anionic amphiphilic polymers of this type are disclosed and prepared, for example, according to U.S. Pat. Nos. 3,915,921 and 4,509,949.

Representative anionic amphiphilic polymers that can be used may further be chosen from polymers formed from a mixture of monomers comprising:

(vii) acrylic acid, an ester of formula (IV) below:

in which $R^1$ is chosen from H and $CH_3$, $R^2$ is chosen from $C_{10}$-$C_{30}$ alkyl radicals, such as alkyl radicals containing from 12 to 22 carbon atoms, and a crosslinking agent; such as polymers derived from 95% to 60% by weight of the acrylic acid (hydrophilic unit), 4% to 40% by weight of $C_{10}$-$C_{30}$ alkyl acrylate (hydrophobic unit), and 0% to 6% by weight of crosslinking polymerizable monomer, or polymers derived from 98% to 96% by weight of the acrylic acid (hydrophilic unit), 1% to 4% by weight of $C_{10}$-$C_{30}$ alkyl acrylate (hydrophobic unit) and 0.1% to 0.6% by weight of crosslinking polymerizable monomer; or (viii) acrylic acid and lauryl methacrylate, such as the polymers formed from 66% by weight of acrylic acid and 34% by weight of lauryl methacrylate.

The crosslinking agent can be a monomer comprising a group

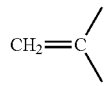

with at least one other polymerizable group whose unsaturated bonds are not conjugated.

Mention may be made, for example, of polyallyl ethers such as polyallylsucrose and polyallylpentaerythritol.

Among said polymers above, mention may be made, for example, of the products sold by the company Goodrich under the trade names Pemulen TR1, Pemulen TR2, Carbopol 1382, and further, for example, Pemulen TR1, and the product sold by the company S.E.P.C. under the name Coatex SX.

Among anionic amphiphilic fatty-chain polymers, mention may also be made, for example, of the ethoxylated copolymer of methacrylic acid/methyl acrylate/alkyl dimethyl-meta-isopropenylbenzylisocyanate sold under the name Viscophobe DB 1000 by the company Amerchol.

The (3) cationic amphiphilic polymers used are, for example, chosen from quaternized cellulose derivatives and polyacrylates comprising amino side groups.

The quaternized cellulose derivatives are, for example, chosen from quaternized celluloses modified with groups comprising at least one fatty chain, such as alkyl, arylalkyl and alkylaryl groups comprising at least 8 carbon atoms, and mixtures thereof, and quaternized hydroxyethylcelluloses modified with groups comprising at least one fatty chain, such as alkyl, arylalkyl and alkylaryl groups comprising at least 8 carbon atoms, and mixtures thereof.

Quaternized and non-quaternized polyacrylates comprising amino side groups have, for example, hydrophobic groups, such as Steareth 20 (polyoxy-ethylenated(20) stearyl alcohol) and ($C_{10}$-$C_{30}$)alkyl PEG-20 itaconate.

The alkyl radicals borne by the above quaternized celluloses and hydroxyethylcelluloses, for example, contain from 8 to 30 carbon atoms.

The aryl radicals, for example, are chosen from phenyl, benzyl, naphthyl and anthryl groups.

Examples of quaternized alkylhydroxyethyl-celluloses comprising $C_8$-$C_{30}$ fatty chains are the products Quatrisoft LM 200, Quatrisoft LM-X 529-18-A, Quatrisoft LM-X 529-18B ($C_{12}$ alkyl) and Quatrisoft LM-X 529-8 ($C_{18}$ alkyl) sold by the company Amerchol, and the products Crodacel QM, Crodacel QL ($C_{12}$ alkyl) and Crodacel QS ($C_{18}$ alkyl) sold by the company Croda.

Examples of polyacrylates comprising amino side chains are the polymers 8781-124B or 9492-103 and Structure Plus from the company National Starch.

Among (4) amphoteric amphiphilic polymers comprising at least one hydrophilic unit and at least one fatty-chain unit, mention may be made, for example, of copolymers of methacrylamidopropyltrimethylammonium chloride/acrylic acid/$C_{10}$-$C_{30}$ alkyl methacrylate, wherein the alkyl radical is, for example, a stearyl radical.

The associative thickeners can have, for example, in solution or in dispersion at a concentration of 1% active material in water, a viscosity, measured using a Rheomat® 180 rheometer at 25° C., of greater than 0.1 ps and further, for example, of greater than 0.2 cp, at a shear rate of 200 $s^{-1}$.

The (a) associative thickener may be an associative polymeric thickener, preferably an associative polyurethane thickener.

The associative polyurethane thickener may be cationic or nonionic.

Among the associative polyurethane thickeners, there may be mentioned the associative polyurethane derivatives such as those obtained by polymerization: about 20% to 70% by weight of a carboxylic acid containing an α,β-monoethylenic unsaturation, about 20 to 80% by weight of a nonsurfactant monomer containing an α,β-monoethylenic unsaturation, about 0.5 to 60% by weight of a nonionic mono-urethane which is the product of the reaction of a monohydroxylated surfactant with a monoethylenically unsaturated monoisocyanate.

The like are described in particular in EP 173109 and more particularly in example 3. More precisely, this polymer is a methacrylic acid/methyl acrylate/dimethyl metaisopropenyl benzyl isocyanate of ethoxylated behenyl alcohol (40EO) terpolymer as an aqueous dispersion at 25%. This product is provided under the reference VISCOPHOBE DB1000 by the company AMERCHOL.

Also suitable are the cationic associative polyurethane thickeners the family of which has been described by the Applicant in French Patent Application No. 0009609. It can be represented more particularly by the following general formula (A): R—X—(P)$_n$-[L-(Y)$_m$]$_r$-L'-(P')$_p$—X'—R' (A) in which: R and R', which are identical or different, represent a hydrophobic group or a hydrogen atom; X and X', which are identical or different, represent a group containing an amine functional group carrying or otherwise a hydrophobic group, or alternatively the group L"; L, L' and L", which are identical or different, represent a group derived from a diisocyanate; P and P', which are identical or different, represent a group containing an amine functional group carrying or otherwise a hydrophobic group; Y represents a hydrophilic group; r is an integer between 1 and 100, preferably between 1 and 50 and in particular between 1 and 25; n, m and p are each independently of the others between 0 and 1000; the molecule containing at least one protonated or quaternized amine functional group and at least one hydrophobic group.

In a very advantageous embodiment, the only hydrophobic groups of these polyurethanes are the groups R and R' at the chain ends.

According to a first preferred embodiment, the associative polyurethane thickener corresponds to the formula (A) in which R and R' both represent independently a hydrophobic group, X, X' each represent a group L", n and p are between 1 and 1000, and L, L', L", P, P', Y and m have the meaning indicated in formula (A).

According to another preferred embodiment of the present invention, the associative polyurethane thickener corresponds to the formula (A) in which R and R' both represent independently a hydrophobic group, X, X' each represent a group L", n and p are equal to 0, and L, L', L", Y and m have the meaning in formula (A) indicated above.

The fact that n and p are equal to 0 means that these polymers do not contain units derived from a monomer containing an amine functional group, incorporated into the polymer during polycondensation. The protonated amine functional groups of these polyurethanes result from the hydrolysis of isocyanate functional groups, in excess, at the chain end, followed by alkylation of the primary amine functional groups formed by alkylating agents containing a hydrophobic group, that is to say compounds of the RQ or R'Q type, in which R and R' are as defined above and Q denotes a leaving group such as a halide, a sulfate and the like.

In accordance with another preferred embodiment of the present invention, the associative polyurethane thickener corresponds to formula (A) in which R and R' both represent independently a hydrophobic group, X and X' both represent independently a group containing a quaternary amine, n and p are equal to zero, and L, L', Y and m have the meaning indicated in formula (A).

The number-average molecular mass of the cationic associative polyurethane thickeners is usually between 400 and 500 000, in particular between 1000 and 400 000, and ideally between 1000 and 300 000 g/mol.

When X and/or X' denote a group containing a tertiary or quaternary amine, X and/or X' may represent one of the following formulae:

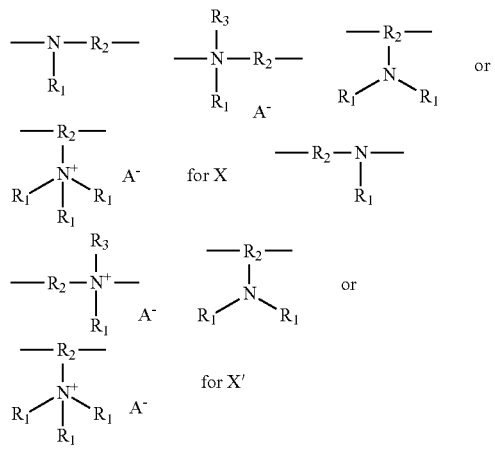

in which:

$R_2$ represents a linear or branched alkylene radical having from 1 to 20 carbon atoms, containing or otherwise a saturated or unsaturated ring, or an arylene radical, it being possible for one or more of the carbon atoms to be replaced by a heteroatom chosen from N, S, O, P;

$R_1$ and $R_3$, which are identical or different, denote a linear or branched, $C_1$-$C_{30}$ alkyl or alkenyl radical, an aryl radical, it being possible for at least one of the carbon atoms to be replaced by a heteroatom chosen from N, S, O, and P;

$A^-$ is a physiologically acceptable counterion.

The groups L, L' and L" represent a group of formula:

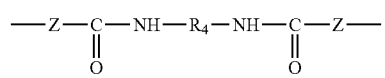

in which:

Z represents —O—, —S— or —NH—; and $R_4$ represents a linear or branched alkylene radical having from 1 to 20 carbon atoms, containing or otherwise a saturated or unsaturated ring, an arylene radical, it being possible for one or more of the carbon atoms to be replaced by a heteroatom chosen from N, S, O and P.

The groups P and P', comprising an amine functional group, may represent at least one of the following formulae:

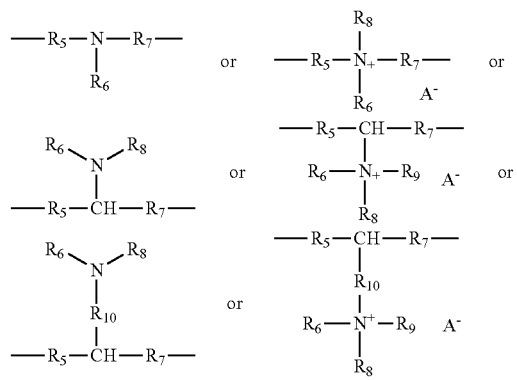

or in which:

$R_5$ and $R_7$ have the same meanings as $R_2$ defined above;

$R_6$, $R_8$ and $R_9$ have the same meanings as $R_1$ and $R_3$ defined above;

$R_{10}$ represents a linear or branched alkylene group, which is optionally unsaturated and which may contain one or more heteroatoms chosen from N, O, S and P;

$A^-$ is a physiologically acceptable counterion.

As regards the meaning of Y, the expression hydrophilic group is understood to mean a polymeric or nonpolymeric water-soluble group. By way of example, there may be mentioned, when polymers are not involved, ethylene glycol, diethylene glycol and propylene glycol. In accordance with a preferred embodiment, in the case of a hydrophilic polymer, there may be mentioned, by way of example, polyethers, sulfonated polyesters, sulfonated polyamides, or a mixture of these polymers. Preferably, the hydrophilic compound is a polyether and in particular a polyethylene oxide or a polypropylene oxide.

The cationic associative polyurethane thickeners of formula (A) are formed from diisocyanates and from various compounds possessing functional groups containing a labile hydrogen. The functional groups containing a labile hydrogen may be alcohol functional groups, primary or secondary amine functional groups or thiol functional groups which give, after reaction with the diisocyanate functional groups, polyurethanes, polyureas and polythioureas, respectively. The term "polyurethanes" of the present invention covers these three types of polymer, namely polyurethanes proper, polyureas and polythioureas and copolymers thereof.

A first type of compounds entering into the preparation of the polyurethane of formula (A) is a compound containing at least one unit containing an amine functional group. This compound may be multifunctional, but preferably the compound is difunctional, that is to say, according to a preferred embodiment, this compound contains two labile hydrogen atoms carried for example by a hydroxyl, primary amine, secondary amine or thiol functional group. It is also possible to use a mixture of multifunctional and difunctional compounds in which the percentage of multifunctional compounds is low.

As indicated above, this compound may contain more than one unit containing an amine functional group. It is then a polymer carrying a repeat of the unit containing an amine functional group.

This type of compound may be represented by one of the following formulae: $HZ-(P)_n-ZH$, or $HZ-(P')_p-ZH$, in which Z, P, P', n and p are as defined above.

By way of examples of a compound containing an amine functional group, there may be mentioned N-methyldiethanolamine, N-tert-butyldiethanolamine, N-sulfoethyldiethanolamine.

The second compound entering into the preparation of the polyurethane of formula (A) is a diisocyanate corresponding to the formula $O=C=N-R_4-N=C=O$ in which $R_4$ is defined above.

By way of example, there may be mentioned methylenediphenyl diisocyanate, methylenecyclohexane diisocyanate, isophorone diisocyanate, toluene diisocyanate, naphthalene diisocyanate, butane diisocyanate, and hexane diisocyanate.

A third compound entering into the preparation of the polyurethane of formula (A) is a hydrophobic compound intended to form the terminal hydrophobic groups of the polymer of formula (A).

This compound consists of a hydrophobic group and a functional group containing a labile hydrogen, for example a hydroxyl, primary or secondary amine, or thiol functional group.

By way of example, this compound may be a fatty alcohol, such as in particular stearyl alcohol, dodecyl alcohol, and decyl alcohol. When this compound contains a polymeric chain, it may be for example a hydroxyl hydrogenated polybutadiene.

The hydrophobic group of the polyurethane of formula (A) may also result from the quaternization reaction of the tertiary amine of the compound containing at least one tertiary amine unit. Thus, the hydrophobic group is introduced by the quaternizing agent. This quaternizing agent is a compound of the RQ or R'Q type, in which R and R' are as defined above and Q denotes a leaving group such as a halide, a sulfate, and the like.

The cationic associative polyurethane thickener may additionally comprise a hydrophilic sequence. This sequence is provided by a fourth type of compound entering into the preparation of the polymer. This compound may be multifunctional. It is preferably difunctional. It is also possible to have a mixture where the percentage of multifunctional compound is low.

The functional groups containing a labile hydrogen are alcohol, primary or secondary amine, or thiol functional groups. This compound may be a polymer terminated at the chain ends by one of these functional groups containing a labile hydrogen.

By way of example, there may be mentioned, when polymers are not involved, ethylene glycol, diethylene glycol and propylene glycol.

In the case of a hydrophilic polymer, there may be mentioned, by way of example, polyethers, sulfonated polyesters, sulfonated polyamides, or a mixture of these polymers. Preferably, the hydrophilic compound is a polyether and in particular a polyethylene oxide or a polypropylene oxide.

The hydrophilic group noted Y in formula (A) is optional. Indeed, the units containing a quaternary or protonated amine functional group may suffice to provide the solubility or water-dispersibility necessary for this type of polymer in an aqueous solution. Although the presence of a hydrophilic group Y is optional, cationic associative polyurethane thickeners are nevertheless preferred which contain such a group.

The associative polyurethane thickener used in the present invention may also be nonionic, in particular nonionic polyurethane-polyethers. The nonionic polyurethane-polyethers may have both at least one hydrophilic moiety and at least one hydrophobic moiety. More particularly, said polymers may contain in their chain both hydrophilic sequences most often of a polyoxyethylenated nature and hydrophobic sequences which may be aliphatic linkages alone and/or cycloaliphatic and/or aromatic linkages.

Preferably, these polyether-polyurethanes comprise at least two lipophilic hydrocarbon chains, having from 6 to 30 carbon atoms, preferably from 6 to 20, separated by a hydrophilic sequence, it being possible for the hydrocarbon chains to be pendent chains or chains at the end of a hydrophilic sequence. In particular, it is possible for one or more pendent chains to be envisaged. In addition, the polymer may comprise a hydrocarbon chain at one end or at both ends of a hydrophilic sequence.

The polyether-polyurethanes may be polyblocks, in particular in triblock form. The hydrophobic sequences may be at each end of the chain (for example: triblock copolymer with hydrophilic central sequence) or distributed both at the ends and in the chain (polyblock copolymers for example). These same polymers may also be in the form of graft units or may be star-shaped.

The associative polyurethane thickener can form a network in water in which the hydrophobic part connects quasi-micelles as shown in FIG. 1.

Therefore, the associative polyurethane thickeners can increase viscosity or consistency of the composition according to the present invention. Thus, after application of the composition according to the present invention, it can recover the original elasticity of the composition quickly.

The nonionic polyether-polyurethanes containing a fatty chain may be triblock copolymers whose hydrophilic sequence is a polyoxyethylenated chain comprising from 50 to 1000 oxyethylenated groups.

The nonionic polyether-polyurethanes comprise a urethane bond between the hydrophilic sequences, hence the origin of the name.

By extension, those whose hydrophilic sequences are linked by other chemical bonds to the hydrophobic sequences are also included among the nonionic polyether-polyurethanes containing a hydrophobic chain.

By way of examples of nonionic polyether-polyurethanes containing a hydrophobic chain which can be used in the present invention, it is also possible to use Rheolate® 205 containing a urea functional group sold by the company RHEOX or else the Rheolates® 208, 204 or 212, as well as Acrysol® 1840.

There may also be mentioned the product ELFACOS T210® containing a $C_{12}$-$C_{14}$ alkyl chain and the product ELFACOS T212® containing a $C_{18}$ alkyl chain from AKZO.

The product DW 1206B® from ROHM & HAAS containing a $C_{20}$ alkyl chain and with a urethane bond, sold at 20% dry matter content in water, may also be used.

It is also possible to use solutions or dispersions of these polymers in particular in water or in an aqueous-alcoholic medium. By way of examples of such polymers, there may be mentioned Rheolate® 255, Rheolate® 278 and Rheolate® 244 sold by the company RHEOX. It is also possible to use the product DW 1206F and DW 1206J provided by the company ROHM & HAAS.

The above-described polyether-polyurethanes which can be used can also be chosen from those described in the article by G Fonnum, J. Bakke and Fk. Hansen-Colloid Polym. Sci 271, 380-389 (1993).

As the above-described polyether-polyurethanes, mention may be made of polyurethane-polyethers comprising in their chain at least one polyoxyethylenated hydrophilic block and at least one of hydrophobic blocks containing at least one sequence chosen from aliphatic sequences, cycloaliphatic sequences, and aromatic sequences.

It may be preferable that the polyurethane-polyethers comprise at least two hydrocarbon-based lipophilic chains having from 8 to 30 carbon atoms, separated by a hydrophilic block, and wherein the hydrocarbon-based chains are chosen from pendent chains and chains at the end of the hydrophilic block.

According to a specific form of the present invention, use will be made of a polyurethane/polyether that may be obtained by polycondensation of at least three compounds comprising (i) at least one polyethylene glycol comprising from 150 to 180 mol of ethylene oxide, (ii) a polyoxyethylenated stearyl alcohol comprising 100 mol of ethylene oxide, and (iii) a diisocyanate.

Such polyurethane/polyethers are sold especially by the company Elementis under the name Rheolate FX 1100® and Rheoluxe 8118, which is a polycondensate of polyethylene glycol containing 136 mol of ethylene oxide, of stearyl alcohol polyoxyethylenated with 100 mol of ethylene oxide and of hexamethylene diisocyanate (HDI) with a weight-average molecular weight of 40000 (INCI name: PEG-136/Steareth-100/HDI Copolymer).

According to another specific form of the present invention, use will be made of a polyurethane/polyether that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate.

Such polyurethane/polyethers are sold in particular by the company Rohm & Haas under the names Aculyn 46® and Aculyn 44®.

Aculyn 46® having the INCI name: PEG-150/Stearyl Alcohol/SMDI Copolymer, is a polycondensate of polyethylene glycol comprising 150 or 180 mol of ethylene oxide, of stearyl alcohol and of methylenebis(4-cyclohexyl isocyanate) (SMDI) at 15% by weight in a matrix of maltodextrin (4%) and water (81%) (INCI name: PEG-150/Stearyl Alcohol/SMDI Copolymer).

Aculyn 44® (PEG-150/Decyl Alcohol/SMDI Copolymer) is a polycondensate of polyethylene glycol comprising 150 or 180 mol of ethylene oxide, of decyl alcohol and of methylenebis(4-cyclohexyl isocyanate) (SMDI) at 35% by weight in a mixture of propylene glycol (39%) and water (26%) (INCI name: PEG-150/Decyl Alcohol/SMDI Copolymer).

As the associative polyurethanes, it may be preferable to use a compound represented by the following formula (1):

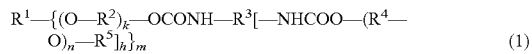

(1)

wherein $R^1$ represents a hydrocarbon group, $R^2$ and $R^4$ independently represent alkylene groups having 2 to 4 carbon atoms, which alkylene groups may be identical or different from each other, or a phenylethylene group, $R^3$ represents a hydrocarbon group, which may optionally have a urethane bond, $R^5$ represents a branched chain or secondary hydrocarbon group, m represents a number of at least 2, h represents a number of at least 1, k represents a number within the range of 1 to 500, and n represents a number within the range of 1 to 200.

The hydrophobically modified polyurethane that is represented by the general formula (1) shown above is obtained by, for example, reacting at least one polyether polyol that is represented by the formula $R^1—[(O—R^2)_k—OH]_m$, at least one polyisocyanate that is represented by the formula $R^3—(NCO)_{h+1}$, and at least one polymonoalcohol that is represented by the formula $HO—(R^4—O)_n—R^5$.

In such cases, $R^1$ to $R^5$ in the general formula (1) are determined by the compounds $R^1—[(O—R^2)_k—OH]_m$, $R^3—(NCO)_{h+1}$ and $HO—(R^4—O)_n—R^5$. The loading ratios among the three compounds are not limited particularly and should preferably be such that the ratio of the isocyanate group derived from the polyisocyanate to the hydroxyl group derived from the polyether polyol and the polyether monoalcohol is selected within the range of NCO/OH of between 0.8:1 and 1.4:1.

The polyether polyol compound that is represented by the formula $R^1—[(O—R^2)_k—OH]_m$ and that may be used preferably for obtaining the associative thickener represented by the general formula (1) may be obtained from addition polymerization of an m-hydric polyol with an alkylene oxide, such as ethylene oxide, propylene oxide, butylene oxide, or epichlorohydrin, or with styrene oxide, and the like.

The polyols should preferably be di- to octa-hydric polyols. Examples of the di- to octa-hydric polyols include dihydric alcohols, such as ethylene glycol, propylene glycol, butylene glycol, hexamethylene glycol, and neopenthyl glycol; trihydric alcohols, such as glycerol, trioxy isobutane, 1,2,3-butanetriol, 1,2,3-pentanetriol, 2-methyl-1,2,3-propanetriol, 2-methyl-2,3,4-butanetriol, 2-ethyl-1,2,3-butanetriol, 2,3,4-pentanetriol, 2,3,4-hexanetriol, 4-propyl-3,4,5-heptanetriol, 2,4-dimethyl-2,3,4-pentanetriol, pentamethylglycerol, pentaglycerol, 1,2,4-butanetriol, 1,2,4-pentanetriol, trimethylolethane, and trimethylolpropane; tetrahydric alcohols, such as pentaerythritol, 1,2,3,4-pentanetetrol, 2,3,4,5-hexanetetrol, 1,2,4,5-pentanetetrol, and 1,3,4,5-hexanetetrol; pentahydric alcohols, such as adonitol, arabitol, and xylitol; hexahydric alcohols, such as dipentaerythritol, sorbitol, mannitol, and iditol; and octahydric alcohols, such as sucrose.

Also, $R^2$ is determined by the alkylene oxide, styrene oxide, or the like, which is subjected to the addition. Particularly, for availability and excellent effects, an alkylene oxide having 2 to 4 carbon atoms, or styrene oxide is preferable.

The alkylene oxide, styrene oxide, or the like, to be subjected to the addition may be subjected to single polymerization, or random polymerization or block polymerization of at least two members. The procedure for the addition may be a conventional procedure. Also, the polymerization degree k may be selected within the range of 0 to 1,000, preferably within the range of 1 to 500, and more preferably within the range of 10 to 200. Further, the ratio of the ethylene group occupying $R^2$ should preferably be within the range of 50 to 100 mass % with respect to the total quantity of $R^2$. In such cases, the associative thickener appropriate for the purposes of the present invention is obtained.

Furthermore, the molecular weight of the polyether polyol compound that is represented by the formula $R^1$—[(O—$R^2$)$_k$—OH]$_m$ should preferably be selected within the range of 500 to 100,000, and should more preferably be selected within the range of 1,000 to 50,000.

The polyisocyanate that is represented by the formula $R^3$—(NCO)$_{h+1}$ and that may be used preferably for obtaining the hydrophobically modified polyether urethane represented by the general formula (1) employed in accordance with the present invention is not limited particularly in so far as the polyisocyanate has at least two isocyanate groups in the molecule. Examples of the polyisocyanates include aliphatic diisocyanates, aromatic diisocyanates, alicyclic diisocyanates, biphenyl diisocyanate, phenylmethane diisocyanate, phenylmethane triisocyanate, and phenylmethane tetraisocyanate.

Also, it is possible to employ dimers and trimers (isocyanurate bonds) of the above-enumerated polyisocyanates. Further, it is possible to employ biuret obtained by a reaction with an amine.

Furthermore, it is possible to employ a polyisocyanate having a urethane bond obtained by a reaction of the aforesaid polyisocyanate compound and a polyol. As the polyol, di- to octa-hydric polyols are preferable, and the above-enumerated polyols are preferable. In cases where a tri- or higher-hydric polyisocyanate is used as the polyisocyanate that is represented by the formula $R^3$—(NCO)$_{n+1}$, it is preferable to employ the aforesaid polyisocyanate having the urethane bond.

The polyether monoalcohol that is represented by the formula HO—($R^4$—O)$_n$—$R^5$ and that may be used preferably for obtaining the hydrophobically modified polyether urethane represented by the general formula (1) employed in accordance with the present invention is not limited particularly in so far as the polyether monoalcohol is a polyether of a straight chain, branched chain, or secondary monohydric alcohol. The polyether monoalcohol may be obtained by addition polymerization of the straight chain, branched chain, or secondary monohydric alcohol with an alkylene oxide, such as ethylene oxide, propylene oxide, butylene oxide, or epichlorohydrin, or with styrene oxide, and the like.

The compound represented by the general formula (1) may be produced by, for example, heating at a temperature of 80 to 90° C. for 1 to 3 hours and thereby causing a reaction to occur in the same manner as that in the ordinary reaction of a polyether and an isocyanate.

As the compound represented by the general formula (1), polyethyleneglycol-240/decyltetradeceth-20/hexamethylene diisocyanate copolymer is preferable. The polyethyleneglycol-240/decyltetradeceth-20/hexamethylene diisocyanate copolymer is referred to also as PEG-240/HDI copolymer bis-decyltetradeceth-20 ether.

According to the present invention, it is preferable that the associative polyurethane thickener be selected from Steareth-100/PEG-136/HDI Copolymer sold by the company Rheox under the name of Rheolate FX 1100, PEG-240/HDI Copolymer Bis-decyltetradeceth-20 ether sold by the company Asahi Denka under the name of Adekanol GT-700, and mixtures thereof.

The amount of the (a) associative thickener in the composition according to the present invention may be from 0.01 to 10% by weight, preferably from 0.1 to 5% by weight, and more preferably from 0.3 to 1% by weight, relative to the total weight of the composition.

(Alkyleneoxide Derivative)

The composition according to the present invention comprises (b) at least one alkyleoxide derivative. Two or more (b) alkyleneoxide derivatives may be used in combination. Thus, a single type of alkyleneoxide derivative or a combination of different types of alkyleneoxide derivatives may be used.

The (b) alkyleneoxide derivative is represented by the following chemical formula (I):

wherein

Z denotes a residue obtained by removing hydroxyl group(s) from a compound having 3 to 9 hydroxyl groups;

AO denotes an oxyalkylene group having 3 to 4 carbon atoms;

EO denotes an oxyethylene group;

BO denotes an oxyalkylene group having 4 carbon atoms;

a denotes 3 to 9;

l, m, and n denote the average addition mole numbers of AO, EO and BO, respectively, and 1≤l≤50, 1≤m≤50 and 0.5≤n≤5;

a weight ratio of AO to EO (AO/EO) ranges from 1/5 to 5/1; and

AO and EO may have been added randomly or in the form of blocks.

In the alkylene oxide derivative represented by formula (I), Z denotes a residue obtained by removing hydroxyl groups from a compound having 3 to 9 hydroxyl groups, and a denotes the number of hydroxyl groups of the compound and denotes 3 to 9. As examples of compounds having 3 to 9 hydroxyl groups, mention may be made of, for example, in the case of a=3, glycerin, and trimethylolpropane; in the case of a=4, erythritol, pentaerythritol, sorbitol, alkylglycosides, and diglycerin; in the case of a=5, xylitol; in the case of a=6, dipentaerythritol, sorbitol, and inositol; in the case of a=8, sucrose, and trehalose; in the case of a=9, maltitol; mixtures thereof; and the like. Preferably, Z denotes a residue obtained by removing hydroxyl group(s) from a compound having 3 to 6 hydroxyl groups, and a satisfies 3≤a≤6. As the compound having 3 to 9 hydroxyl groups, glycerin or trimethylolpropane is preferable, and in particular, glycerin is preferable. In the case of a≤2, poor compatibility with oil components such as fats and oils is exhibited, and blending stability in an oil-based formulation tends to be impaired. In the case of 10≤a, stickiness is caused.

AO denotes an oxyalkylene group having 3 to 4 carbon atoms. As examples thereof, mention may be made of, for example, an oxypropylene group, an oxybutylene group (an oxy-n-butylene group, an oxyisobutylene group, or an oxy-t-butylene group), an oxytrimethylene group, an oxytetramethylene group, and the like. The oxypropylene group and oxybutylene group are preferable, and the oxypropylene group is more preferable.

l denotes the average addition mole number of AO, and satisfies 1≤l≤50, and preferably 2≤l≤20. m denotes the average addition mole number of EO, and satisfies 1≤m≤50, and preferably 2≤m≤20. If l is 0, stickiness occurs. On the other hand, if l exceeds 50, moisturizing effects are decreased. In addition, if m is 0, moisturizing effects are decreased. On the other hand, if m exceeds 50, stickiness occurs.

The weight ratio of AO to EO (AO/EO) ranges from 1/5 to 5/1, and preferably ranges from 1/4 to 4/1. If AO/EO is below 1/5, stickiness occurs. On the other hand, if AO/EO exceeds 5/1, the moisturizing sensation is decreased. The order of adding AO and EO is not particularly specified. AO and EO may have been added randomly or in the form of blocks. In order to obtain superior effects of preventing skin roughness, AO and EO preferably have been added randomly.

BO denotes an oxyalkylene group having 4 carbon atoms. As examples thereof, mention may be made of, for example, an oxybutylene group (an oxy-n-butylene group, an oxy-isobutylene group, or an oxy-t-butylene group), an oxytetramethylene group, and the like. The oxybutylene group is preferable.

n denotes the average addition mole number of BO, and satisfies 0.5<n≤5, preferably 0.8≤n≤3, and more preferably 1≤n≤3. If n is below 0.5, stickiness occurs. On the other hand, if n exceeds 5, moisturizing effects are decreased. In formula (I), it is necessary that $(BO)_n$ bond to the terminal hydrogen atom.

The alkylene oxide derivatives represented by formula (I) can be produced by means of known methods. For example, the alkylene oxide derivatives represented by formula (I) can be obtained by additive-polymerizing ethylene oxide and an alkylene oxide having 3 to 4 carbon atoms to a compound having 3 to 9 hydroxyl groups, and subsequently reacting with an alkylene oxide having 4 carbon atoms. When additive-polymerizing ethylene oxide and an alkylene oxide having 3 to 4 carbon atoms to a compound having 3 to 9 hydroxyl groups, the ethylene oxide and alkylene oxide may be polymerized randomly or in the form of blocks.

Among the alkylene oxide derivatives represented by formula (I), preferable examples of the aforementioned alkylene oxide derivatives include, for example, an alkylene oxide derivative (polyoxybutylene polyoxyethylene polyoxypropylene glycerol) represented by formula (II) shown below:

Gly-{O(PO)$_s$(EO)$_t$-(BO)$_u$H}$_3$        (II)

wherein

Gly denotes a residue obtained by removing hydroxyl groups from glycerin;

PO denotes an oxypropylene group;

EO denotes an oxyethylene group;

s and t denote the average addition mole numbers of PO and EO, respectively, and have a value ranging from 1 to 50;

the weight ratio of PO to EO (PO/EO) ranges from 1/5 to 5/1;

BO denotes an oxyalkylene group having 4 carbon atoms; and u denotes the average addition mole number of BO, and ranges from 0.5 to 5.

The aforementioned alkylene oxide derivative represented by formula (II) can be obtained by adding propylene oxide and ethylene oxide to glycerin, in the ratio of 3 to 150 mole equivalents of each of propylene oxide and ethylene oxide with respect to glycerin, and subsequently, adding the alkylene oxide having 4 carbon atoms in the ratio of 1.5 to 15 mole equivalents thereof with respect to glycerin.

In the case of adding the aforementioned alkylene oxides to glycerin, the addition reactions are carried out with an alkali catalyst, a phase transfer catalyst, a Lewis acid catalyst, or the like. In general, an alkali catalyst such as potassium hydroxide is preferably employed.

Among the alkylene oxide derivatives represented by formula (I), more preferable derivatives are obtained by adding 6 to 10 mol of ethylene oxide and 3 to 7 mol of propylene oxide to glycerin, and subsequently, adding 2 to 4 mol of butylene oxide.

Among the alkylene oxide derivatives represented by formula (I), a further more preferable derivative is polyoxybutylene polyoxyethylene polyoxypropylene glycerol, which is obtained by adding 8 mol of ethylene oxide and 5 mol of propylene oxide to glycerin, and subsequently, adding 3 mol of butylene oxide, and which has an INCI name of PEG/PPG/polybutylene glycol-8/5/3 glycerin. PEG/PPG/polybutylene glycol-8/5/3 glycerin is commercially available as the trade name of WILBRIDE S-753 from NOF Corporation.

The amount of the (b) alkyleneoxide derivative in the composition may be from 0.01 to 10% by weight, preferably from 0.1 to 5% by weight, and more preferably from 0.3 to 1% by weight, relative to the total weight of the composition.

(Nonionic Surfactant with HLB Value of 13.0 or less)

The composition according to the present invention comprises (c) at least one nonionic surfactant, other than ingredient (b), with an HLB value of 13.0 or less. Two or more (c) nonionic surfactants with an HLB value of 13.0 or less except for the ingredient (b) may be used in combination. Thus, a single type of nonionic surfactant or a combination of different types of nonionic surfactant may be used.

The (c) nonionic surfactant with an HLB value of 13.0 or less is different from the (b) aklyleneoxide derivative.

It is preferable that the (c) nonionic surfactant have an HLB value of 12.5 or less, and more preferably, 12.0 or less.

It may be preferable that the (c) nonionic surfactant have an HLB value of 6.0 or more, more preferably 7.0 or more, and even more preferably, 8.0 or more.

If two or more nonionic surfactants are used, the HLB value is determined by the weight average of the HLB values of all the nonionic surfactants. HLB is the ratio between the hydrophilic part and the lipophilic part in the molecule. This term HLB is well known to those skilled in the art and is described in "The HLB system. A time-saving guide to emulsifier selection" (published by ICI Americas Inc., 1984).

The nonionic surfactants are compounds well known in themselves (see, e.g., in this regard, "Handbook of Surfactants" by M. R. Porter, Blackie & Son publishers (Glasgow and London), 1991, pp. 116-178). Thus, they can, for example, be chosen from alcohols, alpha-diols, alkylphenols and esters of fatty acids, these compounds being ethoxylated, propoxylated or glycerolated and having at least one fatty chain comprising, for example, from 8 to 30 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils of plant origin; fatty acid esters of sucrose; fatty acid esters of polyethylene glycol; polyethoxylated fatty acid mono or diesters of glycerol (C$_6$-C$_{24}$)alkylpolyglycosides; N—(C$_6$-C$_{24}$)alkylglucamine derivatives; amine oxides such as (C$_{10}$-C$_{14}$)alkylamine oxides or N—(C$_{10}$-C$_{14}$)acylaminopropylmorpholine oxides; silicone surfactants; and mixtures thereof.

The nonionic surfactants may preferably be chosen from monooxyalkylenated, polyoxyalkylenated, monoglycerolated or polyglycerolated nonionic surfactants. The oxyalkylene units are more particularly oxyethylene or oxypropylene units, or a combination thereof, and are preferably oxyethylene units.

Examples of monooxyalkylenated or polyoxyalkylenated nonionic surfactants that may be mentioned include:

monooxyalkylenated or polyoxyalkylenated (C$_8$-C$_{24}$)alkylphenols, saturated or unsaturated, linear or branched, monooxyalkylenated or polyoxyalkylenated C$_8$-C$_{30}$ alcohols, saturated or unsaturated, linear or branched, monooxyalkylenated or polyoxyalkylenated C$_8$-C$_{30}$ amides, esters of saturated or unsaturated, linear or branched, C$_8$-C$_{30}$ acids and of polyalkylene glycols, monooxyalkylenated or polyoxyalkylenated esters of saturated or unsaturated, linear or branched, C$_8$-C$_{30}$ acids and of sorbitol, saturated or unsaturated, monooxyalkylenated or polyoxyalkylenated plant oils, condensates of ethylene oxide and/or of propylene oxide, inter alia, alone or as mixtures.

The surfactants preferably contain a number of moles of ethylene oxide and/or of propylene oxide of between 1 and 100 and most preferably between 2 and 50. Advantageously, the nonionic surfactants do not comprise any oxypropylene units.

According to one of the embodiments of the present invention, the polyoxyalkylenated nonionic surfactants are chosen from polyoxyethylenated fatty alcohol (polyethylene glycol ether of fatty alcohol) and polyoxyethylenated fatty ester (polyethylene glycol ester of fatty acid).

Examples of polyoxyethylenated fatty alcohol (or C$_8$-C$_{30}$ alcohols) that may be mentioned include the adducts of ethylene oxide with lauryl alcohol, especially those containing from 9 to 50 oxyethylene units and more particularly those containing from 10 to 12 oxyethylene units (Laureth-10 to Laureth-12, as the CTFA names); the adducts of ethylene oxide with behenyl alcohol, especially those containing from 9 to 50 oxyethylene units (Beheneth-9 to Beheneth-50, as the CTFA names); the adducts of ethylene oxide with cetearyl alcohol (mixture of cetyl alcohol and stearyl alcohol), especially those containing from 10 to 30 oxyethylene units (Ceteareth-10 to Ceteareth-30, as the CTFA names); the adducts of ethylene oxide with cetyl alcohol, especially those containing from 10 to 30 oxyethylene units (Ceteth-10 to Ceteth-30, as the CTFA names); the adducts of ethylene oxide with stearyl alcohol, especially those containing from 10 to 30 oxyethylene units (Steareth-10 to Steareth-30, as the CTFA names); the adducts of ethylene oxide with isostearyl alcohol, especially those containing from 10 to 50 oxyethylene units (Isosteareth-10 to Isosteareth-50, as the CTFA names); and mixtures thereof.

As the esters of saturated or unsaturated, linear or branched, C$_8$-C$_{30}$ acids and of polyalkylene glycols, mention may be made of polyoxyethylenated C$_8$-C$_{30}$ fatty ester having a polyoxyethylene moiety derived from 2 to 100 polyoxyethylenes.

Examples of polyoxyethylenated C$_8$-C$_{30}$ fatty esters that may be mentioned include the adducts of ethylene oxide with esters of lauric acid, palmitic acid, stearic acid or behenic acid, and mixtures thereof, especially those containing from 8 to 100 oxyethylene units, such as PEG-8 to PEG-50 laurate (CTFA names: PEG-8 laurate to PEG-50 laurate); PEG-8 to PEG-50 palmitate (CTFA names: PEG-8 palmitate to PEG-50 palmitate); PEG-8 to PEG-50 stearate (CTFA names: PEG-8 stearate to PEG-50 stearate); PEG-8 to PEG-50 palmitostearate; PEG-8 to PEG-50 behenate (CTFA names: PEG-8 behenate to PEG-50 behenate); polyethylene glycol 100 EO monostearate (CTFA name: PEG-100 stearate); and mixtures thereof.

As examples of monoglycerolated or polyglycerolated nonionic surfactants, monoglycerolated or polyglycerolated C$_8$-C$_{40}$ alcohols are preferably used.

In particular, the monoglycerolated or polyglycerolated C$_8$-C$_{40}$ alcohols correspond to the following formula:

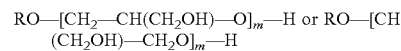
RO—[CH$_2$—CH(CH$_2$OH)—O]$_m$—H or RO—[CH(CH$_2$OH)—CH$_2$O]$_m$—H in which R represents a linear or branched C$_8$-C$_{40}$ and preferably C$_8$-C$_{30}$ alkyl or alkenyl radical, and m represents a number ranging from 1 to 30 and preferably from 1.5 to 10.

As examples of compounds that are suitable in the context of the present invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol may represent a mixture of alcohols in the same way that the value of m represents a statistical value, which means that, in a commercial product, several species of polyglycerolated fatty alcohol may coexist in the form of a mixture.

Among the monoglycerolated or polyglycerolated alcohols, it is preferable to use the C$_8$/C$_{10}$ alcohol containing 1 mol of glycerol, the C$_{10}$/C$_{12}$ alcohol containing 1 mol of glycerol and the C$_{12}$ alcohol containing 1.5 mol of glycerol.

The monoglycerolated or polyglycerolated C$_8$-C$_{40}$ fatty esters may correspond to the following formula:

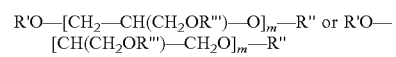
R'O—[CH$_2$—CH(CH$_2$OR''')—O]$_m$—R'' or R'O—[CH(CH$_2$OR''')—CH$_2$O]$_m$—R'' in which each of R', R'' and R''' independently represents a hydrogen atom, or a linear or branched C$_8$-C$_{40}$ and preferably C$_8$-C$_{30}$ alkyl-CO- or alkenyl-CO-radical, with the proviso that at least one of R', R'' and R''' is not a hydrogen atom, and m represents a number ranging from 1 to 30 and preferably from 1.5 to 10.

It may be preferable that the polyglycerolated C$_8$-C$_{40}$ fatty ester have a polyglycerol moiety derived from 2 to 10 glycerols, more preferably from 3 to 6 glycerols, and further more preferably 5 or 6 glycerols.

The polyglycerolated C$_8$-C$_{40}$ fatty ester may be chosen from the mono, di and tri esters of saturated or unsaturated acid, preferably saturated acid, including 8 to 30 carbon atoms, preferably 10 to 30 carbon atoms, and more preferably 12 to 30 carbon atoms, such as lauric acid, oleic acid, stearic acid, isostearic acid, capric acid, and myristic acid.

The polyglycerolated C$_8$-C$_{40}$ fatty acid ester may be selected from the group consisting of PG2 caprate, PG2 dicaprate, PG2 tricaprate, PG2 laurate, PG2 dilaurate, PG2 trilaurate, PG2 myristate, PG2 dimyristate, PG2 trimyristate, PG2 stearate, PG2 distearate, PG2 tristearate, PG2 isostearate, PG2 diisostearate, PG2 triisostearate, PG2 oleate, PG2 dioleate, PG2 trioleare, PG3 caprate, PG3 dicaprate, PG3 tricaprate, PG3 laurate, PG3 dilaurate, PG3 trilaurate, PG3 myristate, PG3 dimyristate, PG3 trimyristate, PG3 stearate, PG3 distearate, PG3 tristearate, PG3 isostearate, PG3 diisostearate, PG3 triisostearate, PG3 oleate, PG3 dioleate, PG3 trioleare, PG4 caprate, PG4 dicaprate, PG4 tricaprate, PG4 laurate, PG4 dilaurate, PG4 trilaurate, PG4 myristate, PG4 dimyristate, PG4 trimyristate, PG4 stearate, PG4 distearate, PG4 tristearate, PG4 isostearate, PG4 diisostearate, PG4 triisostearate, PG4 oleate, PG4 dioleate, PG4 trioleare, PG5 caprate, PG5 dicaprate, PG5 tricaprate, PG5 laurate, PG5 dilaurate, PG5 trilaurate, PG5 myristate, PG5 dimyristate, PG5 trimyristate, PG5 stearate, PG5 distearate, PG5 tristearate, PG5 isostearate, PG5 diisostearate, PG5 triisostearate, PG5 oleate, PG5 dioleate, PG5 trioleare, PG6 caprate, PG6 dicaprate, PG6 tricaprate, PG6 laurate, PG6 dilaurate, PG6 trilaurate, PG6 myristate, PG6 dimyristate, PG6 trimyristate, PG6 stearate, PG6 distearate, PG6 tristearate, PG6 isostearate, PG6 diisostearate, PG6 triisostearate, PG6 oleate, PG6 dioleate, and PG6 trioleare.

According to one of the embodiments of the present invention, the nonionic surfactant may be selected from esters of polyols with fatty acids with a saturated or unsaturated chain containing for example from 8 to 24 carbon atoms, preferably 12 to 22 carbon atoms, and polyoxyalkylenated derivatives thereof, preferably containing from 10 to 200, and more preferably from 10 to 100 oxyalkylene units, such as glyceryl esters of a $C_8$-$C_{24}$, preferably $C_{12}$-$C_{22}$, fatty acid or acids and polyoxyalkylenated derivatives thereof, preferably containing from 10 to 200, and more preferably from 10 to 100 oxyalkylene units; sorbitol esters of a $C_8$-$C_{24}$, preferably $C_{12}$-$C_{22}$, fatty acid or acids and polyoxyalkylenated derivatives thereof, preferably containing from 10 to 200, and more preferably from 10 to 100 oxyalkylene units; sugar (sucrose, maltose, glucose, fructose, and/or alkylglycose) esters of a $C_8$-$C_{24}$, preferably $C_{12}$-$C_{22}$, fatty acid or acids and polyoxyalkylenated derivatives thereof, preferably containing from 10 to 200, and more preferably from 10 to 100 oxyalkylene units; ethers of fatty alcohols; ethers of sugar and a $C_8$-$C_{24}$, preferably $C_{12}$-$C_{22}$, fatty alcohol or alcohols; and mixtures thereof.

As glyceryl esters of fatty acids, glyceryl stearate (glyceryl mono-, di- and/or tristearate) (CTFA name: glyceryl stearate) or glyceryl ricinoleate and mixtures thereof can be cited, and as polyoxyalkylenated derivatives thereof, mono-, di- or triester of fatty acids with a polyoxyalkylenated glycerol (mono-, di- or triester of fatty acids with a polyalkylene glycol ether of glycerol), preferably polyoxyethylenated glyceryl stearate (mono-, di- and/or tristearate), such as PEG-20 glyceryl stearate (mono-, di- and/or tristearate) can be cited.

Mixtures of these surfactants, such as for example the product containing glyceryl stearate and PEG-100 stearate, marketed under the name ARLACEL 165 by Uniqema, and the product containing glyceryl stearate (glyceryl mono- and distearate) and potassium stearate marketed under the name TEGIN by Goldschmidt (CTFA name: glyceryl stearate SE), can also be used.

The sorbitol esters of $C_8$-$C_{24}$ fatty acids and polyoxyalkylenated derivatives thereof can be selected from sorbitan palmitate, sorbitan isostearate, sorbitan trioleate and esters of fatty acids and alkoxylated sorbitan containing for example from 20 to 100 EO, such as for example sorbitan monostearate (CTFA name: sorbitan stearate), sold by the company ICI under the name Span 60, sorbitan monopalmitate (CTFA name: sorbitan palmitate), sold by the company ICI under the name Span 40, and sorbitan tristearate 20 EO (CTFA name: polysorbate 65), sold by the company ICI under the name Tween 65, polyethylene sorbitan trioleate (polysorbate 85) or the compounds marketed under the trade names Tween 20 or Tween 60 by Uniqema.

As esters of fatty acids and glucose or alkylglucose, glucose palmitate, alkylglucose sesquistearates such as methylglucose sesquistearate, alkylglucose palmitates such as methylglucose or ethylglucose palmitate, methylglucoside fatty esters, the diester of methylglucoside and oleic acid (CTFA name: Methyl glucose dioleate), the mixed ester of methylglucoside and the mixture of oleic acid/hydroxystearic acid (CTFA name: Methyl glucose dioleate/hydroxystearate), the ester of methylglucoside and isostearic acid (CTFA name: Methyl glucose isostearate), the ester of methylglucoside and lauric acid (CTFA name: Methyl glucose laurate), the mixture of monoester and diester of methylglucoside and isostearic acid (CTFA name: Methyl glucose sesqui-isostearate), the mixture of monoester and diester of methylglucoside and stearic acid (CTFA name: Methyl glucose sesquistearate) and in particular the product marketed under the name Glucate SS by AMERCHOL, and mixtures thereof can be cited.

As ethoxylated ethers of fatty acids and glucose or alkylglucose, ethoxylated ethers of fatty acids and methylglucose, and in particular the polyethylene glycol ether of the diester of methylglucose and stearic acid with about 20 moles of ethylene oxide (CTFA name: PEG-20 methyl glucose distearate) such as the product marketed under the name Glucam E-20 distearate by AMERCHOL, the polyethylene glycol ether of the mixture of monoester and diester of methyl-glucose and stearic acid with about 20 moles of ethylene oxide (CTFA name: PEG-20 methyl glucose sesquistearate) and in particular the product marketed under the name Glucamate SSE-20 by AMERCHOL and that marketed under the name Grillocose PSE-20 by GOLDSCHMIDT, and mixtures thereof, can for example be cited.

As sucrose esters, saccharose palmito-stearate, saccharose stearate and saccharose monolaurate can for example be cited.

As sugar ethers, alkylpolyglucosides can be used, and for example decylglucoside such as the product marketed under the name MYDOL 10 by Kao Chemicals, the product marketed under the name PLANTAREN 2000 by Henkel, and the product marketed under the name ORAMIX NS 10 by Seppic, caprylyl/capryl glucoside such as the product marketed under the name ORAMIX CG 110 by Seppic or under the name LUTENSOL GD 70 by BASF, laurylglucoside such as the products marketed under the names PLANTAREN 1200 N and PLANTACARE 1200 by Henkel, coco-glucoside such as the product marketed under the name PLANTACARE 818/UP by Henkel, cetostearyl glucoside possibly mixed with cetostearyl alcohol, marketed for example under the name MONTANOV 68 by Seppic, under the name TEGO-CARE CG90 by Goldschmidt and under the name EMULGADE KE3302 by Henkel, arachidyl glucoside, for example in the form of the mixture of arachidyl and behenyl alcohols and arachidyl glucoside marketed under the name MONTANOV 202 by Seppic, cocoylethylglucoside, for example in the form of the mixture (35/65) with cetyl and stearyl alcohols, marketed under the name MONTANOV 82 by Seppic, and mixtures thereof can in particular be cited.

Mixtures of glycerides of alkoxylated plant oils such as mixtures of ethoxylated (200 EO) palm and copra (7 EO) glycerides can also be cited.

The nonionic surfactant according to the present invention preferably contains alkenyl or branched $C_{12}$-$C_{22}$ acyl chain such as oleyl or isostearyl group. More preferably, the nonionic surfactant according to the present invention is PEG-20 glyceryl triisostearate.

According to one of the embodiments of the present invention, the nonionic surfactant may be selected from polyoxyethylenated (1-40 EO) and polyoxypropylenated (1-30 PO) alkyl ($C_{16}$-$C_{30}$) ethers with an HLB value of 13.0 or less.

The polyoxyethylenated (1-40 EO) and polyoxypropylenated (1-30 PO) alkyl ($C_{16}$-$C_{30}$) ethers which may be used as surfactants in the nanoemulsion according to the present invention, may be selected from the group consisting of:

PPG-6 Decyltetradeceth-30; Polyoxyethylene (30) Polyoxypropylene (6) Tetradecyl Ether such as those sold as Nikkol PEN-4630 from Nikko Chemicals Co., PPG-6 Decyltetradeceth-12; Polyoxyethylene (12) Polyoxypropylene (6) Tetradecyl Ether such as those sold as Nikkol PEN-4612 from Nikko Chemicals Co., PPG-13 Decyltetradeceth-24; Polyoxyethylene (24) Polyoxypropylene (13) Decyltetradecyl Ether such as those sold as UNILUBE 50MT-2200B from NOF Corporation, PPG-6 Decyltetradeceth-20; Polyoxyethylene (20) Polyoxypropylene (6) Decyltetradecyl Ether such as those sold as Nikkol PEN-4620 from Nikko Chemicals Co., PPG-4 Ceteth-1; Polyoxyethylene (1) Polyoxypropylene (4) Cetyl Ether such as those sold as Nikkol PBC-31 from Nikko Chemicals Co., PPG-8 Ceteth-1; Polyoxyethylene (1) Polyoxypropylene (8) Cetyl Ether such as those sold as Nikkol PBC-41 from Nikko Chemicals Co., PPG-4 Ceteth-10; Polyoxyethylene (10) Polyoxypropylene (4) Cetyl Ether such as those sold as Nikkol PBC-33 from Nikko Chemicals Co., PPG-8 Ceteth-20; Polyoxyethylene (20) Polyoxypropylene (8) Cetyl Ether such as those sold as Nikkol PBC-44 from Nikko Chemicals Co., and PPG-23 Steareth-34; Polyoxyethylene Polyoxypropylene Stearyl Ether (34 EO) (23 PO) such as those sold as Unisafe 34S-23 from Pola Chemical Industries.

It may be preferable that the polyoxyethylenated (1-40 EO) and polyoxypropylenated (1-30 PO) alkyl ($C_{16}$-$C_{30}$) ethers be (1-40 EO) and polyoxypropylenated (5-30 PO) alkyl ($C_{16}$-$C_{30}$) ethers, which could be selected from the group consisting of PPG-6 Decyltetradeceth-30, PPG-13 Decyltetradeceth-24, PPG-6 Decyltetradeceth-20, PPG-8 Ceteth-20, and PPG-23 Steareth-34.

It may be more preferable that the polyoxyethylenated (1-40 EO) and polyoxypropylenated (1-30 PO) alkyl ($C_{16}$-$C_{30}$) ethers be (15-40 EO) and polyoxypropylenated (5-30 PO) alkyl ($C_{16}$-$C_{24}$) ethers, which could be selected from the group consisting of PPG-6 Decyltetradeceth-30, PPG-13 Decyltetradeceth-24, and PPG-8 Ceteth-20.

According to one of the embodiments according to the present invention, the nonionic surfactant may be selected from copolymers of ethylene oxide and of propylene oxide, in particular copolymers of the following formula:

$$HO(C_2H_4O)_a(C_3H_6O)_b(C_2H_4O)_cH$$

in which a, b and c are integers such that a+c ranges from 2 to 100 and b ranges from 14 to 60, and mixtures thereof.

According to one of the embodiments according to the present invention, the nonionic surfactant may be selected from silicone surfactants such as dimethicone copolyol. Non-limiting mention may be made of those disclosed in documents U.S. Pat. Nos. 5,364,633 and 5,411,744.

The silicone surfactant may preferably be a compound of formula (I):

$$R_1-\underset{\underset{CH_3}{|}}{\overset{\overset{CH_3}{|}}{Si}}O-[\underset{\underset{CH_3}{|}}{\overset{\overset{CH_3}{|}}{Si}}O]_A-[\underset{\underset{R_2}{|}}{\overset{\overset{CH_3}{|}}{Si}}O]_B-\underset{\underset{CH_3}{|}}{\overset{\overset{CH_3}{|}}{Si}}-R_3 \quad (I)$$

in which:

$R_1$, $R_2$ and $R_3$, independently of each other, represent a $C_1$-$C_6$ alkyl radical or a radical $-(CH_2)_x-(OCH_2CH_2)_y-(OCH_2CH_2CH_2)_z-OR_4$, at least one radical $R_1$, $R_2$ or $R_3$ not being an alkyl radical; $R_4$ being a hydrogen, an alkyl radical or an acyl radical;

A is an integer ranging from 0 to 200;

B is an integer ranging from 0 to 50; with the proviso that A and B are not simultaneously equal to zero;

x is an integer ranging from 1 to 6;

y is an integer ranging from 1 to 30;

z is an integer ranging from 0 to 5.

According to one preferred embodiment of the present invention, in the compound of formula (I), the alkyl radical is a methyl radical, x is an integer ranging from 2 to 6 and y is an integer ranging from 4 to 30.

As examples of silicone surfactants of formula (I), mention may be made of the compounds of formula (II):

$$(CH_3)_3SiO-[(CH_3)_2SiO]_A-(CH_3SiO)_B-Si(CH_3)_3 \\ | \\ (CH_2)_2-(OCH_2CH_2)_y-OH \quad (II)$$

in which A is an integer ranging from 20 to 105, B is an integer ranging from 2 to 10 and y is an integer ranging from 10 to 20.

As examples of silicone surfactants of formula (I), mention may also be made of the compounds of formula (III):

$$H-(OCH_2CH_2)_{y'}-(CH_2)_3-[(CH_3)_2SiO]_{A'}-(CH_2)_3 \\ -(OCH_2CH_2)_{y'}-OH \quad (III)$$

in which A' and y are integers ranging from 10 to 20.

Compounds of the present invention which may be used are those sold by the company Dow Corning under the names DC 5329, DC 7439-146, DC 2-5695 and Q4-3667. The compounds DC 5329, DC 7439-146 and DC 2-5695 are compounds of formula (II) in which, respectively, A is 22, B is 2 and y is 12; A is 103, B is 10 and y is 12; A is 27, B is 3 and y is 12.

The compound Q4-3667 is a compound of formula (III) in which A is 15 and y is 13.

It may be preferable that the (c) nonionic surfactant with an HLB value of 13.0 or less be selected from:

(1) (1-40 EO) and polyoxypropylenated (5-30 PO) alkyl ($C_{16}$-$C_{30}$) ethers, and preferably (15-40 EO) and polyoxypropylenated (5-30 PO) alkyl ($C_{16}$-$C_{24}$) ethers;

(2) mono- or polyoxyethylenated fatty ethers/esters, preferably polyoxyethylenated fatty esters, and more preferably polyoxyethylenated $C_8$-$C_{40}$ fatty ester having a polyoxyethylene moiety derived from 2 to 100 polyoxyethylenes;

(3) mono- or polyglycerolated fatty ethers/esters, preferably polyglycerolated fatty esters, and more preferably polyglycerolated $C_8$-$C_{40}$ fatty ester having a polyglycerol moiety derived from 2 to 10 glycerols; and (4) silicone surfactants, preferably dimethicone copolyol.

The amount of the (c) nonionic surfactant with an HLB value of 13.0 or less in the composition may be from 0.01 to 10% by weight, preferably from 0.05 to 5% by weight, and more preferably from 0.1 to 2% by weight, relative to the total weight of the composition.

(Other Ingredients)

The composition according to the present invention may also comprise at least one additional ingredient.

The amount of the additional ingredient(s) is not limited, but may be from 0.1 to 10% by weight relative to the total weight of the composition according to the present invention.

The additional ingredient(s) may be selected from the group consisting of thickeners other than (a) associative thickener; anionic, cationic, nonionic or amphoteric polymers; anionic, cationic or amphoteric surfactants; peptides and derivatives thereof; protein hydrolyzates; swelling agents and penetrating agents; agents for combating hair loss; anti-dandruff agents; natural or synthetic thickeners for oils except for the ingredient (a); suspending agents; sequestering agents; opacifying agents; dyes; sunscreen agents; vitamins or provitamins; fragrances; preserving agents, stabilizers; and mixtures thereof.

The thickeners other than (a) associative thickener include hydrophilic thickeners, for example, carboxyvinylpolymers such as the Carbopol products (carbomers) and cellulose-based derivatives such as hydroxyethylcellulose; polysaccharides and especially gums such as xanthan gum; and mixtures thereof.

The vehicle for the composition according to the present invention is preferably an aqueous medium consisting of water and may advantageously contain one or several cosmetically acceptable organic solvents, which particularly include alcohols, such as ethyl alcohol, isopropyl alcohol, benzyl alcohol and phenylethyl alcohol, or polyols or polyol ethers, such as ethylene glycol monomethyl, monoethyl and monobutyl ethers, propylene glycol or ethers thereof, such as propylene glycol monomethylether, butylene glycol, dipropylene glycol as well as diethylene glycol alkyl ethers, such as diethylene glycol monoethylether or monobutylether and glycerol.

The amount of the (d) water in the composition may be from 50 to 95% by weight, preferably from 60 to 90% by weight, and more preferably from 70 to 90% by weight, relative to the total weight of the composition.

The organic solvent(s) may then be present in a concentration of from 0.1 to 20% by weight, and preferably from 1 to 10% by weight relative to the total weight of the composition.

(Viscosity)

It is preferable that the composition according to the present invention have a viscosity of 530 mPa·s or more, more preferably 550 mPa·s or more, and even more preferably 580 mPa·s or more. The viscosity can be measured with, for example, a viscosimeter proRheo Rheomat R 180 (measuring bob: MK3, measuring cup: MB3, 200 rpm, 10 minutes) at room temperature (25° C.).

It is also preferable that the composition according to the present invention have a viscosity of 50000 mPa·s or less, more preferably 10000 mPa·s or less, and even more preferably 3000 mPa·s or less.

It may be preferable that the composition according to the present invention have a viscosity of from 530 to 50000 mPa·s, more preferably from 550 to 10000 mPa·s, even more preferably from 580 to 3000 mPa·s, and in particular from 600 to 1000 mPa·s.

The composition according to the present invention may preferably be in the form of a gel, and more preferably a transparent gel.

[Cosmetic Use]

The composition according to the present invention may preferably be used as a cosmetic composition. In particular, the composition according to the present invention may be intended for application onto a keratin substance such as the skin, the scalp and/or the lips, preferably the skin. Thus, the composition according to the present invention can be used for a cosmetic process for the skin.

The cosmetic process or cosmetic use for a keratin substance such as skin, according to the present invention comprises, at least, the step of applying onto the keratin substance the composition according to the present invention.

EXAMPLES

The present invention will be described in a more detailed manner by way of examples. However, these examples should not be construed as limiting the scope of the present invention.

Examples 1-6 and Comparative Examples 1-5

The following compositions according to Examples 1-6 and Comparative Examples 1-5, shown in Table 1, were prepared by mixing the ingredients shown in Table 1. The numerical values for the amounts of the ingredients shown in Table 1 are all based on "% by weight" as active raw materials.

TABLE 1

|  | Ex. 1 | Ex. 2 | Ex. 3 | Ex. 4 | Ex. 5 | Ex. 6 | Comp. Ex. 1 | Comp. Ex. 2 | Comp. Ex. 3 | Comp. Ex. 4 | Comp. Ex. 5 |
| --- | --- | --- | --- | --- | --- | --- | --- | --- | --- | --- | --- |
| Water | q.s. 100 | q.s. 100 | q.s. 100 | q.s. 100 | q.s. 100 | q.s. 100 | q.s. 100 | q.s. 100 | q.s. 100 | q.s. 100 | q.s. 100 |
| Glycerin | 3 | 3 | 3 | 3 | 3 | 3 | 3 | 3 | 3 | 3 | 3 |
| Dipropyleneglycol | 1 | 1 | 1 | 1 | 1 | 1 | 1 | 1 | 1 | 1 | 1 |
| Butyleneglycol | 5 | 5 | 5 | 5 | 5 | 5 | 5 | 5 | 5 | 5 | 5 |
| Chlorphenesin | 0.27 | 0.27 | 0.27 | 0.27 | 0.27 | 0.27 | 0.27 | 0.27 | 0.27 | 0.27 | 0.27 |
| Phenoxyethanol | 0.5 | 0.5 | 0.5 | 0.5 | 0.5 | 0.5 | 0.5 | 0.5 | 0.5 | 0.5 | 0.5 |
| Sodium citrate | 0.03 | 0.03 | 0.03 | 0.03 | 0.03 | 0.03 | 0.03 | 0.03 | 0.03 | 0.03 | 0.03 |
| Citric acid | 0.016 | 0.016 | 0.016 | 0.016 | 0.016 | 0.016 | 0.016 | 0.016 | 0.016 | 0.016 | 0.016 |
| Carbomer | 0.2 | 0.2 | 0.2 | 0.2 | 02 | 0.2 | 0.2 | 0.2 | 0.2 | 0.2 | 0.2 |
| Potassium hydroxide | 0.08 | 0.08 | 0.08 | 0.08 | 0.08 | 0.08 | 0.08 | 0.08 | 0.08 | 0.08 | 0.08 |
| PPG-6 Decyltetradeceth-30 (HLB = 12) | 0.3 | 0.3 | 0.3 | — | — | — | 0.3 | — | — | — | 0.3 |
| PEG-8 Stearate (HLB = 10.8) | — | — | — | 0.3 | — | — | — | — | — | — | — |
| Dimethicone Copolyol (HLB = 10) | — | — | — | — | 0.3 | — | — | — | — | — | — |
| Polyglyceryl-5 Myristate (HLB = 12.2) | — | — | — | — | — | 0.3 | — | — | — | — | — |

TABLE 1-continued

|  | Ex. 1 | Ex. 2 | Ex. 3 | Ex. 4 | Ex. 5 | Ex. 6 | Comp. Ex. 1 | Comp. Ex. 2 | Comp. Ex. 3 | Comp. Ex. 4 | Comp. Ex. 5 |
|---|---|---|---|---|---|---|---|---|---|---|---|
| PEG-60 Hydrogenated castor oil (HLB = 14) | — | — | — | — | — | — | — | — | 0.3 | — | — |
| PPG-4 Ceteth-20 (HLB = 6.5) | — | — | — | — | — | — | — | — | — | 0.3 | — |
| PEG-240/HDI Copolymer bis-decyltetradeceth-20 ether | 0.5 | — | 1 | 0.5 | 0.5 | 0.5 | 0.5 | 0.5 | 0.5 | 0.5 | — |
| Steareth-100/PEG-136/HDI copolymer | — | 0.5 | — | — | — | — | — | — | — | — | 0.5 |
| PEG/PPG/Polybutylene glycol-8/5/3 glycerin | 1 | 1 | 2 | 1 | 1 | 1 | — | 1 | 1 | 1 | — |

[Evaluation 1]

The compositions according to Examples 1-6 and Comparative Examples 1-5 were evaluated as follows.

(Soaping)

Each of 9 panelists applied each of the compositions according to Examples 1-3 and Comparative Examples 1-5 in the same amount onto the skin by spreading and massaging the composition on the skin in order to visually evaluate soaping of the composition.

Good: No soaping was observed.
Poor: Soaping was observed.
The results are shown in Table 2.

TABLE 2

|  | Ex. 1 | Ex. 2 | Ex. 3 | Comp. Ex. 1 | Comp. Ex. 2 | Comp. Ex. 3 | Comp. Ex. 4 | Comp. Ex. 5 |
|---|---|---|---|---|---|---|---|---|
| Soaping | Good | Good | Good | Poor | Good | Good | Good | Poor |

[Evaluation 2]

(Viscosity)

The viscosity of each of the compositions according to Examples 1 and 4-6, and Comparative Examples 1-4 in the same amount was measured by proRheo Rheomat R 180 (measuring bob: MK3, measuring cup: MB3, 200 rpm, 10 minutes) at room temperature. Each composition was evaluated in accordance with the following criteria.

Viscosity of 550 mPa·s or more: Good
Viscosity of less than 550 mPa·s: Poor
The results are shown in Table 3.

TABLE 3

|  | Ex. 1 | Ex. 4 | Ex. 5 | Ex. 6 | Comp. Ex. 1 | Comp. Ex. 2 | Comp. Ex. 3 | Comp. Ex. 4 |
|---|---|---|---|---|---|---|---|---|
| Viscosity | Good | Good | Good | Good | Poor | Poor | Good | Good |

[Evaluation 3]

(Slimy Feeling)

9 panelists applied each of the compositions according to Example 1 and 4-6, and Comparative Examples 1, 3 and 4 in the same amount onto the skin, and scored slimy feeling in accordance with the following criteria.

5: Completely no slimy feeling
4: Not slimy
3: Not very slimy
2: Very slimy
1: Excessively slimy
Average score of 3 or more: Good
Average score of less than 3: Poor
The results are shown in Table 4.

(Stickiness)

9 panelists applied each of the compositions according to Example 1 and 4-6, and Comparative Examples 1, 3 and 4 in the same amount onto the skin, and scored stickiness in accordance with the following criteria.

5: Completely no stickiness
4: Not sticky
3: Not very sticky
2: Very sticky
1: Excessively sticky
Average score of 3 or more: Good
Average score of less than 3: Poor
The results are shown in Table 4.

(Penetration Feeling)

9 panelists applied each of the compositions according to Example 1 and 4-6, and Comparative Examples 1, 3 and 4 in the same amount onto the skin, and scored penetration feeling in accordance with the following criteria.

5: Very fast penetration
4: Fast penetration
3: Not slow penetration
2: Slow penetration
1: Very slow penetration
Average score of 3 or more: Good
Average score of less than 3: Poor
The results are shown in Table 4.

TABLE 4

|  | Ex. 1 | Ex. 4 | Ex. 5 | Ex. 6 | Comp. Ex. 1 | Comp. Ex. 3 | Comp. Ex. 4 |
|---|---|---|---|---|---|---|---|
| Slimy Feeling | Good | Good | Good | Good | Poor | Poor | Poor |
| Stickiness | Good | Good | Good | Good | Poor | Poor | Poor |
| Penetration Feeling | Good | Good | Good | Good | Poor | Good | Good |

The compositions according to Examples 1-3 can prevent soaping, and the compositions according to Examples 1 and 4-6 also have excellent texture (no slimy feeling, no stickiness and good penetration feeling), as well as good viscosity.

On the other hand, the compositions according to Comparative Examples 1 and 5 cannot prevent soaping. The compositions according to Comparative Examples 1 and 2 have poor viscosity. The compositions according to Comparative Examples 3 and 4 have poor texture. Accordingly, the compositions according to Comparative Examples 1-6 cannot have all the properties of (1) prevention of soaping, (2) good viscosity, and (3) excellent texture. On the other hand, the compositions according to Examples 1-6 can have all the above properties (1) to (3) simultaneously.

Thus, it is clear that only the compositions according to the present invention can prevent soaping, while they can achieve an excellent texture and good viscosity.

The invention claimed is:

1. A composition, comprising:
   (a) at least one associative thickener chosen from nonionic associative polyurethane/polyether comprising at least one hydrophilic moiety and at least one hydrophobic moiety in an amount ranging from 0.1% to 5% by weight, relative to the total weight of the composition;
   (b) at least one alkyleneoxide derivative according to formula (I) below:

wherein:
      Z is a residue obtained by removing hydroxyl groups from glycerin;
      AO is an oxyalkylene group having 3 to 4 carbon atoms;
      EO is an oxyethylene group;
      BO is an oxyalkylene group having 4 carbon atoms;
      a is an integer ranging from 3 to 9;
      l, m, and n are the average addition mole numbers of AO, EO, and BO, respectively, wherein l ranges from about 1 to about 50, m ranges from about 1 to about 50, and n ranges from about 0.5 to about 5;
      a weight ratio of AO to EO (AO:EO) ranges from about 1:5 to about 5:1; and
      optionally, AO and EO are added randomly or in the form of blocks,
   wherein the at least one alkyleneoxide derivative is present in an amount ranging from 0.1% to 5% by weight, relative to the total weight of the composition;
   (c) at least one nonionic surfactant, other than the at least one alkyleneoxide derivative, with an HLB value of 13.0 or less in an amount ranging from 0.05% to 5% by weight, relative to the total weight of the composition; and
   (d) water,
   wherein the at least one associative thickener includes PEG-240/HDI copolymer bis-decyltetradeceth-20 ether, steareth-100/PEG-136/HDI copolymer, or a mixture thereof:
   wherein the at least one alkyleneoxide derivative includes at least PEG/PPG/Polybutylene glycol-8/15/3; and
   wherein the at least one nonionic surfactant is chosen from polyoxyethylenated (15-40 EO) and polyoxypropylenated (5-30 PO) alkyl ($C_{16}$-$C_{24}$) ethers.

2. The composition of claim 1, wherein the at least one associative thickener is present in an amount ranging from about 0.3% to about 1% by weight, relative to the total weight of the composition.

3. The composition of claim 1, wherein the at least one alkyleneoxide derivative is present in an amount ranging from about 0.5% to about 2% by weight, relative to the total weight of the composition.

4. The composition of claim 1, wherein the at least one nonionic surfactant is present in an amount ranging from about 0.1% to about 2% by weight, relative to the total weight of the composition.

5. The composition of claim 1, wherein the water is present in an amount ranging from about 50% to about 95% by weight, relative to the total weight of the composition.

6. The composition of claim 1, wherein the water is present in an amount ranging from about 70% to about 90% by weight, relative to the total weight of the composition.

7. The composition of claim 1, wherein the viscosity of the composition is at least about 530 mPa's or more.

8. The composition of claim 1, wherein the composition is in the form of a gel.

9. A cosmetic method for improving skin texture or moisturizing skin, comprising:
   applying to a keratin substance a composition comprising:
      (a) at least one associative thickener chosen from nonionic associative polyurethane/polyether comprising at least one hydrophilic moiety and at least one hydrophobic moiety in an amount ranging from 0.1% to 5% by weight, relative to the total weight of the composition;
      (b) at least one alkyleneoxide derivative corresponding to formula (I) below:

wherein:
         Z is a residue obtained by removing hydroxyl groups from glycerin;
         AO is an oxyalkylene group having 3 to 4 carbon atoms;
         EQ is an oxyethylene group;
         BO is an oxyalkylene group having 4 carbon atoms;
         a is an integer ranging from 3 to 9:
         l, m, and n is the average addition mole numbers of AO, EO, and BO, respectively, wherein l ranges from about 1 to about 50, m ranges from about 1 to about 50, and n ranges from about 0.5 to about 5;
         a weight ratio of AO to EO (AO:EO) ranges from about 1:5 to about 5:1; and
         optionally, AO and EO are added randomly or in the form of blocks,
      wherein the at least one alkyleneoxide derivative is present in an amount ranging from 0.1% to 5% by weight, relative to the total weight of the composition;
      (c) at least one nonionic surfactant, other than the at least one alkyleneoxide derivative, with an HLB value of 13.0 or less in an amount ranging from 0.05% to 5% by weight, relative to the total weight of the composition; and
      (d) water,
      wherein the at least one associative thickener includes PEG-240/HDI copolymer bis-decyltetradeceth-20 ether, steareth-100/PEG-136/HDI copolymer, or a mixture thereof;
      wherein the at least one alkyleneoxide derivative includes at least PEG/PPG/Polybutylene glycol-8/15/3; and wherein the at least one nonionic surfactant is chosen from polyoxyethylenated (15-40 EO) and polyoxypropylenated (5-30 PO) alkyl $C_{16}$-$C_{21}$ ethers.

10. The cosmetic method according to claim 9, wherein the at least one associative thickener is present in the composition in an amount ranging from about 0.3% to about 1% by weight, relative to the total weight of the composition.

11. The cosmetic method according to claim 9, wherein the at least one alkyleneoxide derivative is present in the composition in an amount ranging from about 0.5% o to about 2% by weight, relative to the total weight of the composition.

12. The cosmetic method according to claim 9, wherein the at least one nonionic surfactant is present in the composition in an amount ranging from about 0.1% to about 2% by weight, relative to the total weight of the composition.

13. The cosmetic method according to claim 9, wherein the water is present in the composition in an amount ranging from about 50% to about 95% by weight, relative to the total weight of the composition.

14. The cosmetic method according to claim 9, wherein the water is present in the composition in an amount ranging from about 70% to about 90% by weight, relative to the total weight of the composition.

15. The cosmetic method according to claim 9, wherein the viscosity of the composition is at least about 530 mPa·s or more.

16. The cosmetic method according to claim 9, wherein the composition is in the form of a gel.

\* \* \* \* \*